United States Patent [19]

Wilson

[11] Patent Number: 5,004,461

[45] Date of Patent: Apr. 2, 1991

[54] METHODS FOR RENDERING PLASTICS THROMBORESISTANT AND PRODUCT

[76] Inventor: Joseph E. Wilson, 9827 Brockbank, #136, Dallas, Tex. 75220

[21] Appl. No.: 327,686

[22] Filed: Mar. 23, 1989

[51] Int. Cl.$^5$ .............................................. A61M 5/32
[52] U.S. Cl. .................................................... 604/265
[58] Field of Search ................. 604/266, 265; 623/11; 523/105, 112

[56] References Cited

U.S. PATENT DOCUMENTS

| | | | |
|---|---|---|---|
| 3,566,874 | 3/1971 | Shepherd et al. | 604/265 |
| 3,625,741 | 12/1971 | Stoy | 604/265 |
| 3,861,396 | 1/1975 | Vaillancourt et al. | 604/265 |
| 4,451,568 | 5/1984 | Schneider et al. | 623/1 |
| 4,542,169 | 9/1985 | Costerton | 604/265 |
| 4,554,317 | 11/1985 | Behar et al. | 604/304 |
| 4,581,028 | 4/1986 | Fox | 604/265 |
| 4,605,564 | 8/1986 | Kulla et al. | 604/265 |
| 4,612,337 | 9/1986 | Fox | 604/265 |
| 4,642,104 | 2/1987 | Sakamoto | 604/265 |
| 4,863,444 | 9/1989 | Blömer | 604/265 |
| 4,950,256 | 8/1990 | Luther | 604/265 |

*Primary Examiner*—C. Fred Rosenbaum
*Assistant Examiner*—Sharon Rose
*Attorney, Agent, or Firm*—Charles D. Gunter

[57] ABSTRACT

Provides antithrombotic agents which can be bonded to plastic to provide thromboresistant materials and a method for performing the bonding process. Further provides thromboresistant materials for medical devices used in contact with blood or blood products such as artificial hearts, heart lung machines, kidney dialysis machines, dialysis exchangers, pacemakers, vascular graft tubing, microporous membrane blood oxygenators, intra-aortic balloons, ultra-filtration membranes, blood bags, soft or hard tissue prostheses, cathaters, sutures, artificial organs, and the like.

8 Claims, No Drawings

METHODS FOR RENDERING PLASTICS THROMBORESISTANT AND PRODUCT

BACKGROUND OF THE INVENTION

Since about 1950 a number of medical devices which make contact with the blood of living persons have been developed, manufactured, and used clinically. A partial list would include the pacemaker, arterial graft, prosthetic heart valve, artificial heart, hip prosthesis, heart lung machine, and kidney dialysis machine. The growing artificial organ market in the United States serves several hundred thousand patients at present, and amounts to several billions of dollars annually.

A major problem with artificial organs is that their surfaces are foreign to the blood and tend to initiate red cell destruction, denaturation of proteins, and the coagulation of blood to form clots (thrombogenesis). Of these, the problem of thrombus formation is probably the most severe because of the lethal nature of a suddenly curtailed blood supply to vital organs.

Little was known about the mechanism of blood coagulation until 1905, when P. Morawitz proposed a scheme that remained virtually unchanged until the 1930's. Essentially his concept was the following:

I. prothrombin + activating factors→thrombin

II. fibrinogen + thrombin→fibrin

The conversion of one of the blood proteins, fibrinogen, into a jelly-like solid polymer, fibrin, is one of the major processes in thrombus formation. Later research showed that blood coagulation is a process of great complexity, involving a "coagulation cascade" of reactions which progressively activate a sequence of enzymes known as "factors".

The blood platelets (thrombocytes) also play an important role in thrombus formation, after first being activated by contact with a foreign substance such as plastic. Each activated platelet tends to adhere to the plastic surface and to adjacent platelets forming aggregates. Such clumps or aggregates of platelets, with interwoven strands of fibrin polymer, make up the bulk of the thrombus or clot.

A number of treatments have been devised to render plastics thromboresistant (resistant to clotting), and many promising materials have been developed. However, none of these materials has been completely satisfactory for use in such applications as the artificial heart, kidney, or lung. Such applications would not be possible at present without the use of systemic anticoagulants such as heparin, warfarin, and various antiplatelet agents. At the same time, systemic anticoagulation is not a satisfactory answer because of control problems and the danger of hemorrhage. The administration of any type of anticoagulant into the patient's blood is of short-term effectiveness because the anticoagulant is dissipated by the body.

Blood-contact plastics coated with heparin-containing formulations have been tried, but such coatings are washed away by the blood. Heparin ionically bound to a plastic surface is not permanent, but is eventually removed by the blood flow. Covalently bound heparin has the advantage of permanence, but any type of heparinized surface may lead to thrombocytopenia (J. C. Nelson, Arch. Intern. Med., 138, 548 (1978)), and evidence has been found that heparin induces arterial embolism (R. A. Baird, J. Bone Jt. Surg. Am., 59A, 1061 (1977)). Surface-bound heparin on blood-contact prosthetic devices has been observed to cause a profound shortening of platelet survival time (G. L. Schmer, Trans. Am. Soc. Artif. Intern. Organs, 22, 654 (1976)).

SUMMARY OF THE INVENTION

An object of this invention is to provide novel antithrombotic agents which can be covalently (permanently) bonded to plastics to produce thromboresistant materials, and a convenient method for carrying out the bonding process.

A further object of this invention is to provide thrombo-resistant materials for medical devices used in contact with blood or blood products, such as artificial hearts, heart lung machines, kidney dialysis machines, dialysis exchangers, pacemakers, vascular graft tubing, microporous membrane blood oxygenators, intra-aortic balloons, ultrafiltration membranes, blood bags, soft or hard tissue prostheses, catheters, sutures, and artificial organs.

A preferred technique of previous investigators has been the periodic administration of antithrombotic agents to the patient orally or by intravenous injection. This is inconvenient because the treatment has only a short-term beneficial effect and must soon be repeated. In contrast, the technique described in the present invention provides covalent and essentially permanent bonding of the antithrombotic agent to the plastic, thus giving a product which has a long-term usefulness limited only by the stability of the bound antithrombotic agent. The technique described herein restricts the antithrombotic agent to the (foreign) surface of the plastic, so that the inhibitory effect of the agent is exercised at the exact location where the platelets become activated by surface contact and also at the exact location where the coagulation cascade is initiated.

The venous injection technique allows the blood to carry the injected antithrombotic agent to all parts of the body. In the practice of the present invention the agent is covalently bound to the plastic device and prevented from spreading to other parts of the body and possibly causing harmful side effects. For the same reason, the toxicity of the antithrombotic agent is a much less critical factor in the practice of this invention.

DESCRIPTION OF THE PREFERRED EMBODIMENTS

1. Preparation of Samples for Testing

The first step in sample preparation is the radiation grafting of a suitable monomer on the polymer sample, using a cobalt-60 source of gamma rays. A monomer is selected bearing a linkage group which can be reacted later with the antithrombotic agent selected for bonding to the plastic (see below). A solution of the purified monomer and the polymeric sample to be grafted is placed in a Pyrex reaction capsule and connected to a high vacuum system. The monomer solution is freed of oxygen by freeze-thaw cycling while evacuating, using a dry ice trap on the reaction capsule. Next the reaction capsule containing polymer sample and deoxygenated grafting solution is frozen down with dry ice, sealed from the vacuum line while pumping, and placed in the cobalt-60 source in the selected position for irradiation. After irradiating to the desired gamma ray dosage, the polymeric sample is removed from the reaction capsule and placed in a suitable stirred solvent for two days. The purpose of this extraction is to remove any homopolymer formed within the sample.

The grafted polymeric sample bearing the selected linkage group is next reacted with a solution of the antithrombotic agent that is to be bonded to the sample. If an epoxy type monomer is to be linked with a hydroxyl-bearing antithrombotic agent, a small amount of pyridine catalyst is added to the reaction solution. The reaction is well known and takes place readily:

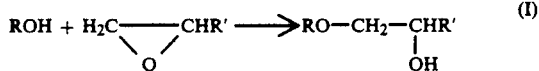

The grafted sample is placed in the solution of antithrombotic agent and allowed to react for a time at room temperature, the amount of agent bonding to the sample increasing with the reaction time.

The reaction of antithrombotic agent with the grafted sample is simple to carry out, involves no dangerous or corrosive chemicals, and is run at room temperature under mild concitions that do not damage or degrade the substrate polymer. The amount of agent bonded to the polymer is readily controllable, and experience indicates that two or three agents can be bonded efficiently in any preferred order.

Although the examples to be cited describe the use of this grafting technique with polysilicone only, it can also be used with other polymers of biomedical interest such as polyurethane, polyethylene, polyvinyl chloride, etc. After grafting, other polymers can be bound to antithrombotic agents by suitable modification of the reaction technique described herein for grafted polysilicone.

The above discussion mentions the treatment of articles of tubular form only, but it is not intended to limit use of the method to tubing. Antithrombotic agents may be covalently bound by the described technique to articles of any shape or form including films, sheets, rods, and devices of proper shape for use in artificial organs, blood handling equipment, or bodily implants.

Also, the antithrombotic agents described in this invention need not be covalently bound to the substrate polymer by the method described above, but may be covalently bound by any other suitable method, such as the bonding of a carboxyl group to an aminated polymer by carbodiimide reagent (A. K. Dincer, Chem. Eng. Commun., 30, 155 (1984)), bonding of a hydroxyl group to a polymer having an isocyanate group (B. D. Halpern, Adv. Chem., 27, 133 (1967)), bonding of a hydroxyl group to an aminated polymer by the use of cyanuric chloride (G. Grode, Proceedings of Artificial Heart Program Conference, page 19 (1969)), etc.

2. Testing of Samples for Thromboresistance

The samples prepared as described above have been tested for thromboresistance in the dog. Prior to thromboresistance testing, each tubular sample is stirred for a day in a suitable solvent to extract any antithrombotic agent which is not chemically bound to the sample but only adsorbed on or dissolved in the sample. Each sample is also sterilized by subjection to an exposure dose of approximately 3,000 roentgens in the cobalt-60 irradiator. On the day prior to the scheduled animal test, each sample is placed in Ringer's lactate solution and equilibrated for approximately 24 hours.

Using the dog as the experimental animal each tubular test sample is made part of an artery-to-artery shunt. The treated sample and the control sample are subjected to blood flow simultaneously, and allowed to remain in position for a six-hour period. In carrying out the test, a large dog (15–25 kg) is anesthetized with sodium pentobarbital (30 mg/kg) and placed on its back on the operating table. The femoral artery of each hind leg is isolated for placement of a polysilicone shunt. A shunt (20 cm in length) is inserted into each artery with one end inserted into the proximal artery and the other into the distal portion of the same artery. The tubing used for the shunt is 1.65 mm in inside diameter and 4.95 mm in outside diameter. A 38 mm segment of polysilicone tubing is placed within each shunt, with the control (untreated) tube segment being used in the one femoral, while the experimental treated tube segment is used in the contralateral artery.

After six hours the anesthetized dog is euthanized with potassium chloride and the shunts are removed. The segments of control and treated tubing are removed from the shunts. The segments are rapidly placed in a fixative solution. They are then cut in half, and the clot formed in each half is scraped off onto a piece of weighed paper and allowed to dry for 30 minutes at room temperature. After 30 minutes the clot is weighed.

Care is taken that the clot from the tubular test segment and from its control are dried for identical lengths of time under identical conditions. Each tubular test sample measures 1.65 mm I.D. and 4.93 mm O.D. and is 38 mm long. The small internal diameter was chosen intentionally so as to provide a severe test of thromboresistance.

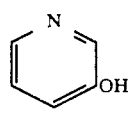

FIG. 1.

3-Hydroxypyridine.

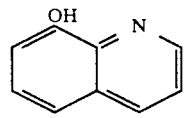

FIG. 2.

8-Hydroxyquinoline.

-continued
FIG. 3.

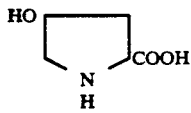

L-Hydroxyproline.

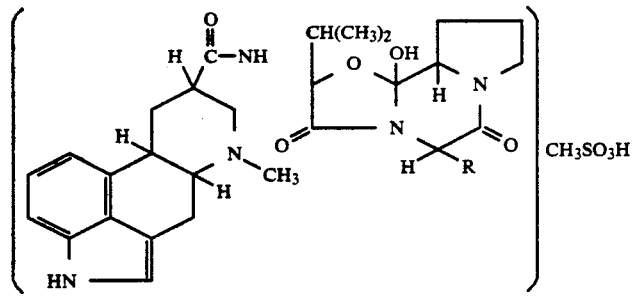

dihydroergocornine    R = —CH(CH$_3$)$_2$
dihydroergocristine   R = —CH$_2$—C$_6$H$_5$
dihydro-α-ergocryptine R = —CH$_2$—CH(CH$_3$)$_2$
dihydro-β-ergocryptine R = —CH(CH$_3$)CH$_2$CH$_3$ FIG. 4. Ergoloid mesylates. An equiproportional mixture of dihydroergocornine methane sulfonate, dihydroergocristine methane sulfonate and α- and β-dihydroergocryptine methane sulfonate in the ratio of 1.5-2.5:1.0. Sold as an α-adrenergic blocker to treat impaired mental function in the elderly under the trade names Circanol, Dacoren, Ergoplus, Orphol, Progeril, Trigot, and Hydergine (Merck Index).

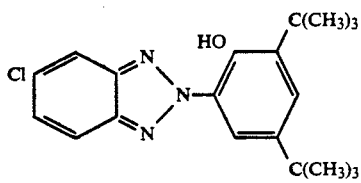

FIG. 5. 2-(3',5'-Di-t-butyl-2'-hydroxyphenyl)-5-chlorobenzotriazole. Sold under the trade name of Tinuvin 327 and used as a light stabilizer for plastics.

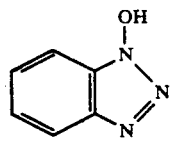

FIG. 6. 1-Hydroxybenzotriazole.

EXAMPLE 1

A standard size polysilicone tube (Sample 40×) was radiation grafted as described above. The monomer used, 2,3-epoxypropylacrylate (EPA), was purified by passage through a column of Dehibit-100 (Polysciences, Inc.). Prior to using the Dehibit-100 it was washed by passing water, methanol, and benzene successively through the column in accordance with routine practice.

The grafting solution consisted of benzene/monomer in a 40/60 ratio by volume. The polysilicone sample was placed in the reaction capsule, covered with grafting solution, and pumped down to remove oxygen as described above. The sealed reaction capsule containing sample and grafting solution was positioned in the irradiator and subjected to an exposure dose of about 16,000 roentgens of gamma rays. After grafting the sample was removed from the reaction capsule, extracted by stirring in warm tetrahydrofuran (THF) for 48 hours, and dried to constant weight in a desiccator. The weight gain indicated that an amount of EPA equal to 11.54% of original sample weight had been grafted on the sample.

The next step involved the linkage of the selected antithrombotic agent, 3-hydroxypyridine (3HP), with the epoxy groups of the grafted sample (see FIG. 1). The reaction solution contained 0.20 gram 3HP, 7.0 ml water, 4.0 ml THF, and 1.0 ml pyridine (catalyst). The grafted sample was covered with the reaction solution in a small test tube, stoppered, and allowed to stand for 78 hours at room temperature to allow the hydroxyl/epoxy linkage to occur. The reacted sample was stirred 24 hours in THF to remove any unreacted 3HP, and then dried to constant weight. The observed weight gain indicated an amount of 3HP equal to 5.84% of original sample weight reacted with the epoxy groups of the sample.

After sterilization, the sample bound to 3HP was tested for thromboresistance as described above by making it part of an artery-to-artery shunt in a dog for 6 hours. The weight of thrombus deposition in the control tube and in the tube bound to 3HP was measured by the technique described above. Thrombus deposition on the control tube amounted to 0.0623 gram compared to 0.0357 gram on the tube bound to 3HP, corresponding to a reduction of 43% in thrombus deposition due to the bound 3HP.

EXAMPLE 2

Using the technique described in Example 1, a polysilicone tube (Sample 41×) of standard size was radiation grafted with purified EPA monomer, employing a benzene/EPA ratio of 40/60 and an exposure dose of about 20,000 roentgens of gamma rays. The weight gain of the sample after extraction and drying to constant weight indicated an amount of EPA equal to 10.61% of original sample weight had been grafted on the sample.

The grafted sample was placed in a solution of 0.10 gram 8-hydroxyquinoline (8HQ), 7.0 ml THF, 4.0 ml water, and 1.0 ml pyridine, and allowed to stand 48 hours at room temperature (see FIG. 2). After the sample was extracted and dried to constant weigth, the weight gain indicated a reaction with an amount of 8HQ equal to 3.99% of original sample weight had taken place.

After sterilization, the sample was made part of an artery-to-artery shunt in the canine test procedure. Thrombus deposited on the control tube weighed 0.097 gram as compared to 0.035 gram on the tube bound to 8HQ, indicating a reduction of 64% in thrombus deposition caused by the bound 8HQ.

EXAMPLE 3

Again using the technique of Example 1, a polysilicone tube (Sample 43×) of standard size was radiation grafted using a grafting solution having a benzene/EPA ratio of 40/60 and an exposure dose of about 23,000 roentgens. Weight gain of the sample after extraction and drying indicated an amount of EPA equal to 11.15% of original sample weight grafted on the sample.

The grafted sample was placed in a solution of 0.10 gram hydroxyproline (HPR), 7.0 ml THF, 4.0 ml water, and 1.0 ml pyridine, and allowed to stand 120 hours at room temperature (see FIG. 3). After extraction and drying the weight gain of the sample indicated reaction with a weight of HPR equal to 3.41% of the original sample weight.

After sterilization, the sample was made part of an artery-to-artery shunt in the usual canine test. Thrombus deposited on the control tube weighed 0.035 gram as compared to 0.012 gram on the tube bound to HPR, indicating a reduction of 66% in thrombus deposition caused by the bound HPR.

EXAMPLE 4

Using the technique described in Example 1, a polysilicone tube (Sample 46×) of standard size was radiation grafted using a grafting solution having a benzene/EPA ratio of 40/60 and an exposure dose of about 25,000 roentgens. Weight gain of the sample after extraction and drying indicated an amount of EPA grafted on the sample equal to 14.76% of the original sample weight.

The grafted sample was placed in a solution of 7.0 ml THF, 4.0 ml water, 1.0 ml pyridine, and 0.10 gram of the composition shown in FIG. 4. The composition in FIG. 4 is sold by several companies under trade names such as Circanol, Hydergine, Dacoren, Ergoplus, Orphol, Progeril, and Trigot. It was called to stand in the solution for 66 hours at room temperature. After extraction and drying, of the sample, the weight gain indicated a reaction with an amount of the composition in FIG. 4 equal to 5.59% of original sample weight had taken place.

After sterilization, the sample was made part of an artery-to-artery shunt in the usual canine test. Thrombus deposited on the control tube weighed 0.0357 gram as compared to only 0.0187 gram on the treated tube, indicating a reduction of 48% in thrombus deposition caused by bonding the sample to the composition shown in FIG. 4.

EXAMPLE 5

Using the technique of Example 1, a polysilicone tube (Sample 56×) of the usual size was radiation grafted employing a grafting solution with a benzene/EPA ratio of 40/60 and an exposure dose of about 20,000 roentgens. The weight gain of the sample after extraction and drying showed an amount of EPA equal to 10.24% of original sample weight grafted on the sample.

The grafted sample was placed in a solution of 0.10 gram of 2-(3',5'-t-butyl-2'-hydroxyphenyl)-5-chlorobenzotriazole (sold commercially as Tinuvin 327), 7.0 ml THF, 4.0 ml water, and 1.0 ml pyridine, and allowed to stand 72 hours at room temperature (see FIG. 5). After extraction and drying the weight gain of the sample indicated reaction with a weight of Tinuvin equal to 7.39% of the original sample weight.

After sterilization, the sample was made part of an artery-to-artery shunt in the customary canine test. Thrombus deposited on the control tube weighed 0.0271 gram compared to 0.0121 gram on the tube bound to Tinuvin, indicating a reduction of 56% in thrombus deposition caused by the bound Tinuvin.

EXAMPLE 6

Two standard size tubes of polysilicone (Samples A and B) were used without any antithrombotic treatment in a special control experiment. The usual canine test for thrombus deposition was carried out, with the Sample A shunt in the right femoral artery and the Sample B shunt in the left femoral artery in the same dog for the identical period of time for each sample. The weight of thrombus deposited on Sample A and B was 0.0295 and 0.0304 gram, respectively. There is only a three percent difference between these two weights. This close duplication contrasts with the examples where the treated sample showed a large reduction in thrombus deposition compared to the untreated control sample.

In considering the examples comparing a treated and untreated sample, it should be noted that the absolute size of the thrombus deposition is not important. The absolute weight of thrombus deposited is strongly dependent on the size and health of the dog, and is also influenced by other uncontrolled variables. The important thing to note is the difference between the treated and untreated sample, because these two samples are always tested in the same dog for an identical time period under identical conditions.

EXAMPLE 7

Employing the method of Example 1, a polysilicone tube (sample 60×) of standard size was radiation grafted using a grafting solution with a benzene/EPA ratio of 40/60 and an exposure dose of approximately 23,000 roentgens. The usual procedure indicated an amount of EPA grafted on the sample equal to 9.23% of the original sample weight.

The grafted sample was placed in a solution containing 0.10 gram 1-hydroxybenzotriazole (HBT), 7.0 ml THF, 4.0 ml water, and 1.0 ml pyridine, and allowed to stand 72 hours at room temperature. Using the standard method of extraction and drying to constant weight, the weight gain of the sample indicated reaction with an amount of HBT equal to 5.77% of original sample weight (see FIG. 6).

After sterilizing the sample it was made part of an artery-to-artery shunt in the standard canine test described previously. The weight of thrombus deposited on the control tube was 0.0236 gram compared to 0.0185 gram deposited on the tube bonded to HBT, showing a reduction of 22% in thrombus deposition caused by the bound HBT.

What is claimed is:

1. A thromboresistant polymeric article for use in contact with blood or blood products, the polymeric article comprising:
a polymeric body formed with at least one exposed surface for contacting blood or blood products, the polymeric body having bonded thereto an antithrombotic agent selected from the group consisting of 3-hydroxypyridine, 8-hydroxyquinoline, L-hydroxyproline, 2-(3,5-di-t-butyl-2-hydroxyphenyl)-5-chlorobenzotriazole, 1-hydroxybenzotriazole, and the compound which comprises an equiproportional mixture of dihydroergocornine methane sulfonate, dihydroergocristine methane sulfonate and $\alpha$- and $\beta$-dihydroergocryptine methane sulfonate in the ratio of 1.5–2.5:1.0.

2. The thromboresistant polymeric article of claim 1, wherein the polymer selected for forming the polymeric body is selected from the group consisting of polysilicone, polyethylene, polyamide, polyvinyl chloride, polyolefin, polyisoprene and butadiene/styrene copolymers.

3. The thromboresistant polymeric article of claim 2, wherein the polymeric body is selected from the group consisting of blood oxygenator tubing, blood oxygenator membrane, vascular graft tubing, catheters, sutures, blood bag, intra-aortic balloons, ultrafiltration membrane, soft tissue prothesis, hard tissue prothesis, artificial heart and artificial organs.

4. A thromboresistant polymeric article for use in contact with blood or blood products, the polymeric article comprising:
a polymeric body having at least one exposed surface for contacting blood or blood products, the polymer being prepared by radiation grafting chains of an epoxypropyl acrylate thereto, followed by reaction of the epoxy groups present with the hydroxyl groups of an antithrombotic agent selected from the group consisting of 3-hydroxypyridine, 8-hydroxyquinoline, L-hydroxyproline, 2-(3,5-di-t-butyl-2-hydroxyphenyl)-5-chlorobenzotriazole, 1-hydroxybenzotriazole, and the compound which comprises an equiproportional mixture of dihydroergocornine methane sulfonate, dihydroergocristine methane sulfonate and $\alpha$- and $\beta$-dihydroergocryptine methane sulfonate in the ratio of 1.5–2.5:1.0, resulting in covalent bonding of the antithrombotic agent to the exposed surface of the polymeric body.

5. A method of forming a thromboresistant polymeric article for use in contact with blood or blood products, the polymeric article being comprised of a polymeric body formed with at least one exposed surface for contacting blood or blood products, the method comprising the steps of:
selecting an antithrombotic agent for permanent bonding to the polymeric article, the antithrombotic agent being selected from the group consisting of 3-hydroxypyridine, 8-hydroxyquinoline, L-hydroxyproline, 2-(3,5-di-t-butyl-2-hydroxyphenyl)-5-chlorobenzotriazole, 1-hydroxybenzotriazole, and the compound which comprises an equiproportional mixture of dihydroergocornine methane sulfonate, dihydroergocristine methane sulfonate and $\alpha$- and $\beta$-dihydroergocryptine methane sulfonate in the ratio of 1.5–2.5:1.0;
selecting a suitable monomer having a reactive linkage adapted to react with the antithrombotic agent to chemically bond the antithrombotic agent to the polymeric article;
grafting the monomer having the reactive linkage to the polymeric article; and
reacting the antithrombotic agent with the reactive linkages of the grafted monomer to thereby covalently bond the antithrombotic agent to the polymeric article.

6. A method of forming a thromboresistant polymeric article for use in contact with blood or blood products, the polymeric article being comprised of a polymeric body formed with at least one exposed surface for contacting blood or blood products, the method comprising the steps of:
selecting an antithrombotic agent for permanent bonding to the polymeric article, the antithrombotic agent being selected from the group consisting of 3-hydroxypyridine, 8-hydroxyquinoline, L-hydroxyproline, 2-(3,5-di-t-butyl-2-hydroxyphenyl)-5-chlorobenzotriazole, 1-hydroxybenzotriazole, and the compound which comprises an equiproportional mixture of dihydroergocornine methane sulfonate, dihydroergocristine methane sulfonate and $\alpha$- and $\beta$-dihydroergocryptine methane sulfonate in the ratio of 1.5–2.5:1.0, the antithrombotic agent being characterized as having reactive hydroxyl groups;
radiation grafting chains of epoxypropyl acrylate onto the polymeric article, the epoxypropyl acrylate being characterized as having reactive epoxy linkages adapted to react with the reactive hydroxyl groups of the antithrombotic agent to thereby chemically bond the antithrombotic agent to the polymeric article;
reacting the antithrombotic agent with the reactive linkages of the grafted epoxypropyl acrylate to thereby covalently bond the antithrombotic agent to the polymeric article.

7. The method of forming a thromboresistant polymeric article of claim 6, wherein the polymer selected for forming the polymeric body is selected from the group consisting of polysilicone, polyethylene, polyamide, polyvinyl chloride, polyolefin, polyisoprene and butadiene/styrene copolymers.

8. The method of forming a thromboresistant polymeric article of claim 7, wherein the polymeric body is selected from the group consisting of blood oxygenator tubing, blood oxygenator membrane, vascular graft tubing, catheters, sutures, blood bags, intra-aortic balloons, ultrafiltration membrane, soft tissue prothesis, hard tissue prothesis, artificial heart and artificial organs.

* * * * *